United States Patent
Eliu et al.

[11] Patent Number: 5,969,204
[45] Date of Patent: Oct. 19, 1999

[54] PROCESS FOR THE PRODUCTION OF DISTYRYL-BIPHENYL COMPOUNDS

[75] Inventors: Victor Eliu, Lörrach, Germany; Werner Kanert, Hegenheim, France; Peter Baumeister, Flüh, Switzerland; Julia Völkel, Grenzach-Wyhlen, Germany

[73] Assignee: Ciba Specialty Chemicals Corporation, Tarrytown, N.Y.

[21] Appl. No.: 08/994,219

[22] Filed: Dec. 19, 1997

[30] Foreign Application Priority Data

Dec. 20, 1996 [GB] United Kingdom .................. 9626554

[51] Int. Cl.$^6$ .......................... C07C 2/74; C07C 5/09; C07C 2/02; C07C 4/02
[52] U.S. Cl. ..................... 585/406; 585/435; 585/508; 585/651
[58] Field of Search ..................... 585/406, 435, 585/508, 657

[56] References Cited

U.S. PATENT DOCUMENTS

| | | | |
|---|---|---|---|
| 3,984,399 | 10/1976 | Weber et al. | 260/240 |
| 5,145,991 | 9/1992 | Weber et al. | 562/87 |
| 5,231,223 | 7/1993 | Bader et al. | 562/87 |
| 5,516,932 | 5/1996 | Beller et al. | 560/104 |

FOREIGN PATENT DOCUMENTS

| | | |
|---|---|---|
| 0364403 | 4/1990 | European Pat. Off. |
| 0584043 | 2/1994 | European Pat. Off. |

*Primary Examiner*—Mukund J. Shah
*Assistant Examiner*—Tamthom N. Truong
*Attorney, Agent, or Firm*—Kevin T. Mansfield

[57] ABSTRACT

A process for the production of compounds useful as fluorescent whitening agents of formula:

(1) [structure: phenyl-(X)n—CH=CH—phenyl(Z)—phenyl(Z)—CH=CH—phenyl-(Y)n]

in which X and Y, are as defined herein and n is 1 or 2, comprises

A) diazotising one mole of an amine of formula:

[structure: phenyl-(X)n—NH$_2$]

(2A) to produce a diazonium compound of the formula:

[structure: phenyl-(X)n—N$_2^\oplus$—G$_1^\ominus$]

(2) in which G$_1$ is a counter ion; and diazotising one mole of an amine of formula:

[structure: phenyl-(Y)n—NH$_2$]

(3A) to produce a diazonium compound having the formula:

[structure: phenyl-(Y)n—N$_2^\oplus$—G$_1^\ominus$]

(3); and

B) reacting one mole of a divinyl compound having the formula:

[structure: H$_2$C=HC—phenyl(Z)—phenyl(Z)—CH=CH$_2$]

(4) with one mole of a compound having the formula (2) and with one mole of a compound having the formula (3), in the presence of an inorganic or organic palladium salt, or a mixture thereof, as catalyst-precursor.

36 Claims, No Drawings

PROCESS FOR THE PRODUCTION OF DISTYRYL-BIPHENYL COMPOUNDS

The present invention relates to a process for the production of fluorescent whitening agents and, in particular, to a process for the production of distyryl-biphenyl fluorescent whitening agents.

The compounds of formula:

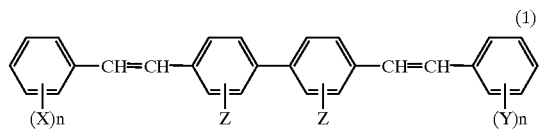

(1)

in which X and Y, independently, are hydrogen, halogen, $NO_2$, $CF_3$, CN, $C_1$–$C_4$alkyl, $C_1$–$C_4$alkoxy, COO—$C_1$–$C_4$alkyl, CO—$C_1$–$C_4$alkyl, NH-($C_1$–$C_4$alkyl), N($C_1$–$C_4$alkyl)$_2$, NH($C_1$–$C_4$alkyl-OH), N($C_1$–$C_4$alkyl-OH)$_2$, COOH or $SO_3H$ or an ester or amide thereof, or COOM or $SO_3M$ in which M is Na, K, Ca, Mg, ammonium, mono-, di-, tri- or tetra-$C_1$–$C_4$alkylammonium, mono-, di- or tri-hydroxyalkylammonium or ammonium that is di- or tri-substituted with a mixture of $C_1$–$C_4$alkyl and $C_1$–$C_4$hydroxyalkyl groups; Z is hydrogen, $C_1$–$C_4$alkyl, $C_1$–$C_4$alkoxy, $CF_3$, halogen, $SO_3H$ or $SO_3M$ in which M has its previous significance; and n is 1 or 2;

are known fluorescent whitening agents or are precursors therefor.

Some of the compounds of formula (1) have been described in U.S. Pat. No. 3,984,399. In U.S. Pat. No. 3,984,399, a process is disclosed for the production of the disclosed compounds of formula (1) comprising reacting a compound having the formula:

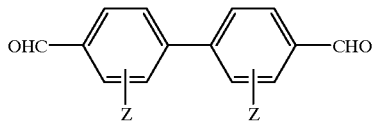

with one mole of a compound having the formula:

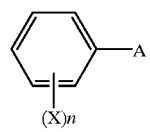

and with one mole of a compound having the formula:

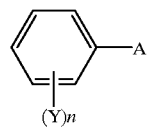

in which X, Y and n have their previous significance, and A is a group selected from —$CH_2PO(OR)_2$, —$CH_2PO(R)(OR)$, —$CH_2PO(R)_2$ and —$CH=P(R)_3$, in which R is, e.g., $C_1$–$C_6$alkyl.

More recently, in EP-508,264, a process for the production of symmetrical compounds of formula (1) has been described comprising reacting a tetrazonium compound having the formula:

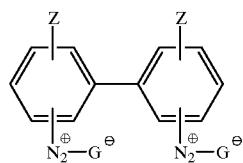

in which Z has its previous significance and G is a sulfate or bisulfate anion, with two moles of a monovinyl compound having the formula:

$R_1$—CH=$CH_2$ in which $R_1$, inter alia, is optionally substituted $C_6$–$C_{10}$aryl. The reaction is conducted in the presence of an inorganic or organic palladium salt, or a mixture thereof, as catalyst, and in water, an alcohol or a mixture thereof, as solvent.

A new route to the compounds of formula (1) has now been found which is simpler and more ecologically attractive than that described in U.S. Pat. No. 3,984,399 and which gives higher yields than those obtained according to the process disclosed in EP-508,264.

Accordingly, the present invention provides a process for the production of a compound of formula:

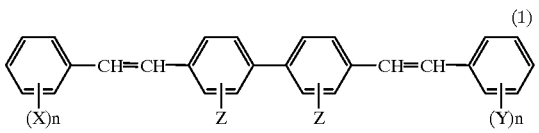

(1)

in which X and Y, independently, are hydrogen, halogen, $NO_2$, $CF_3$, CN, $C_1$–$C_4$alkyl, $C_1$–$C_4$alkoxy, COO—$C_1$–$C_4$alkyl, CO—$C_1$–$C_4$alkyl, NH—($C_1$–$C_4$alkyl), N($C_1$–$C_4$alkyl)$_2$, NH($C_1$–$C_4$alkyl-OH), N($C_1$–$C_4$alkyl-OH)$_2$, COOH or $SO_3H$ or an ester or amide thereof, or COOM or $SO_3M$ in which M is Na, K, Ca, Mg, ammonium, mono-, di-, tri- or tetra-$C_1$–$C_4$alkylammonium, mono-, di- or tri-hydroxyalkylammonium or ammonium that is di- or tri-substituted with a mixture of $C_1$–$C_4$alkyl and $C_1$–$C_4$hydroxyalkyl groups;

Z is hydrogen, $C_1$–$C_4$alkyl, $C_1$–$C_4$alkoxy, $CF_3$, halogen (F, Cl, Br, I), $SO_3H$ or $SO_3M$ in which has its previous significance; and n is 1 or 2; comprising A) diazotising one mole of an amine of formula:

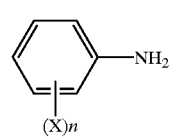

(2A)

in which X and n have their previous significance, to produce a diazonium compound having the formula:

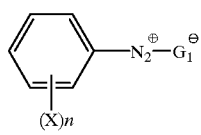

(2)

in which X and n have their previous significance and $G_1$ is a counter ion; and diazotising one mole of an amine of formula:

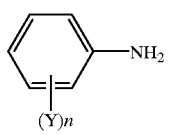

(3A)

in which Y and n have their previous significance, to produce a diazonium compound having the formula:

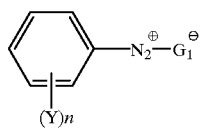

(3)

in which Y, n and $G_1$ have their previous significance; and

B) reacting one mole of a divinyl compound having the formula:

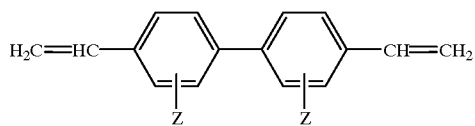

(4)

in which Z has its previous significance, with one mole of a compound having the formula (2) and with one mole of a compound having the formula (3), in the presence of an inorganic or organic palladium salt, or a mixture thereof, as catalyst-precursor.

It is advantageous to conduct step B) of the process without the intermediate isolation of the reactants of formula (2) and (3).

In a modification of the process of the present invention, steps A) and B) may be conducted simultaneously by controlled addition of the respective reactants.

In the compounds of formula (1), preferably X and Y, independently, are hydrogen, cyano, COOM or $SO_3M$ in which M has its previous significance, and preferably Z is hydrogen and n is 1. If the substituents X or Y are negatively charged, then the resulting diazonium salt of formula (2) or (3) may be present as an internal salt.

In the compounds of formula (2) or (3), preferably $G_1$ is $H_2PO_4^-$, $HPO_4^{2-}$, $NO_3^-$, $CF_3COO^-$, $^-OOC-COO^-$ (oxalate), $Cl_3CCOO^-$, $ClCH_2COO^-$, $I^-$, $Cl^-$, $Br^-$, $F^-$, $ClO_4^-$, $PF_6^-$, $BF_4^-$, $Oac^-$, $HSO_4^-$, $SO_4^{2-}$, $CH_3(C_6H_4)SO_3^-$ and $CH_3SO_3^-$, especially $H_2PO_4^-$, $Cl_3CCOO^-$, $ClCH_2COO^-$, $PF_6^-$, $BF_4^-$, $Oac^-$, $HSO_4^-$, $SO_4^{2-}$, $CH_3(C_6H_4)SO_3^-$ and $CH_3SO_3^-$.

Preferably, the compound (2) is identical to the compound (3) so that the compound of formula (1) obtained according to the process of the present invention is symmetrical.

The starting materials of formula (4) are known compounds and may be produced by methods known per se. The preferred compound of formula (4) is 4,4'-divinyl-biphenyl which may be produced, for example, by dehydrogenation of 4,4'-diethyl-biphenyl. This dehydrogenation reaction has been described, for example, in JP 08003079-A.

The diazonium compounds having the formula (2) or (3) are known compounds and may be produced by methods known per se. The diazonium compounds may be formed in situ or added as a salt of formula (2) or (3). The in situ formation may also be conducted in the presence of the olefins of formula $CHR_2=CHR_3$ in which $R_2$ is H, F, Cl, Br or $-COOR_4$ (in which $R_4$ is H or $C_1-C_4$alkyl) and $R_3$ is $-COO(C_1-C_4alkyl)$, $-COR_4$ or $C_1-C_2$alkyl optionally substituted by halogen, e.g. by the addition of alkyl nitrites such as t-butyl nitrite, as described in J. Org. Chem. vol.46, pp. 4885–4888 (1981).

For example, the said diazonium compounds may be produced by reacting the corresponding amines with an alkali metal nitrite, an alkyl nitrite or nitrosylsulfonic acid, optionally in the presence of an acid, in aqueous or in organic solution. If the diazotisation is conducted in organic solution, it is preferred that the water, produced as a by-product of the diazotisation reaction, is removed either as it is formed, or prior to the reaction step B). The removal of such water may be conveniently conducted by effecting the diazotisation in the presence of water-binding materials such as acetic anhydride, sodium sulfate, calcium chloride or molecular sieves.

When n is 1, examples of the amino component precursors of the diazo salt starting materials of formula (2) or (3) include, e.g., aniline, 2-, 3- or 4-chloro-aniline, 2-, 3- or 4-bromo-aniline, 2-, 3- or 4-iodo-aniline, 2-, 3- or 4-trifluoromethyl-aniline, 2-, 3- or 4-nitrilo-aniline, 2-, 3- or 4-methyl-aniline, 2-, 3- or 4-ethyl-aniline, 2-, 3- or 4-n-propyl-aniline, 2-, 3- or 4-n-butyl-aniline, 2-, 3- or 4-methoxy-aniline, 2-, 3- or 4-ethoxy-aniline, 2-, 3- or 4-n-propoxy-aniline, 2-, 3- or 4-n-butoxy-aniline, 2-, 3- or 4-amino-benzoic acid or its methyl, -ethyl-, n-propyl or n-butyl ester, 2-, 3- or 4-amino-acetophenone, 2-, 3- or 4-methylamino-aniline, 2-, 3- or 4-ethylamino-aniline, 2-, 3- or 4-hydroxyethyleneamino-aniline, 2-, 3- or 4-di(hydroxyethyleneamino)-aniline and 2-, 3- or 4-aminobenzene sulfonic acid. In the cases of 2-, 3- or 4-aminobenzoic acid and 2-, 3- or 4-aminobenzene sulfonic acid, these acids may be used in the form of their respective salts in which the cation M has its previous significance and is preferably sodium.

When n is 2, examples of the amino component precursors of the diazo salt starting materials of formula (3) or (4) include, e.g., 3- or 4-aminobenzo-1,2-dinitrile, 3- or 4-aminobenzene-1,2-dicarboxylic acid or its dimethyl, -diethyl-, di-n-propyl or di-n-butyl ester, aminobenzene-2,4-disulfonic acid, aminobenzene-3,5-disulfonic acid or aminobenzene-2,5-disulfonic acid. In the cases of 3- or 4-aminobenzene-1,2-dicarboxylic acid and aminobenzene-2,4-disulfonic acid, aminobenzene-3,5-disulfonic acid or aminobenzene-2,5-disulfonic acid, these acids may be used in the form of their respective salts in which the cation M has its previous significance and is preferably sodium.

The preferred compound of formula (3) and (4) is 2-, 3- or 4-aminobenzene sulfonic acid. The preferred product of the process of the present invention has the formula:

(101)

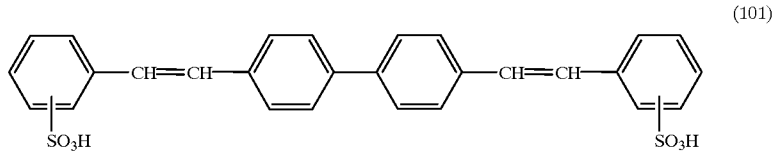

or an alkali metal salt, especially the sodium salt thereof.

The palladium catalyst precursor used in step A) may be generated, in situ or ex situ, by reduction of a palladium (II) compound, optionally in the presence of a salt such as sodium acetate, and optionally in the presence of suitable ligand-forming or colloid-stabilising compounds. Suitable palladium (II) compounds include $PdCl_2$, $PdBr_2$, $Pd(NO_3)_2$, $H_2PdCl_4$, $Pd(OOCCH_3)_2$, $[PdCl_4]Na_2$, $[PdCl_4]Li_2$, $[PdCl_4]K_2$, palladium(II)acetylacetonate, dichloro-(1,5-cyclooctadiene)palladium(II), dichlorobis-(acetonitrile)palladium(II), dichlorobis-(benzonitrile)palladium(II), π-allylpalladium(II)chloride dimer, bis-(π-methallyl palladium(II)chloride) and π-allylpalladium(II) acetylacetonate. Suitable ligand-forming compounds are, for example, olefins having the formula $CHR_2$=$CHR_3$ in which $R_2$ is H, F, Cl, Br or —$COOR_4$ (in which $R_4$ is H or $C_1$–$C_4$alkyl) and $R_3$ is —$COO(C_1$–$C_4$alkyl), —$COR_4$ or $C_1$–$C_2$alkyl optionally substituted by halogen; dibenzylideneacetone (dba) optionally substituted with halogen (F, Cl or Br), $SO_3M$ (in which M has its previous significance), $C_1$–$C_4$alkyl or $C_1$–$C_4$alkoxy in the benzene rings; phosphites such as those of formula $P(OR_5)$ in which $R_5$ is e.g. phenyl, $C_1$–$C_6$alkyl or a partially or perfluorinated $C_1$–$C_6$alkyl; or CO. The substituents in the benzene rings are preferably linked in the para-positions of the benzene rings. The ligand-forming compounds may be used alone or in combinations of at least two compounds. The production of the palladium catalyst precursor used in step A) and the reaction conditions used in step B), are described in more detail in EP-584,043.

Suitable reducing agents are, e.g., CO, $H_2$, formates, primary or secondary $C_1$–$C_8$alkanols, hydrazine, amines, mixtures of CO with alkanols or water, or the ligating olefine per se.

The catalyst may be added as $Pd(dba)_2$, $Pd(dba)_3$.solvent $Pd_2(dba)_3$ or $Pd_2(dba)_3$.solvent. The dba ligand may be optionally substituted in the aromatic part as described above.

Optionally, the catalyst may be added as Pd on a suitable support such as charcoal or $Al_2O_3$ (EP-606,058).

Preferably the palladium catalyst is used in an amount of 0.01 to 5 mole %, based on the diazonium salt of formula (2) or (3).

After completion of the process according to the present invention, the palladium catalyst is preferably recovered for re-use, by methods which are well-known.

The process according to the present invention may be effected in water, as solvent, in which case, preferably the palladium compound catalyst used contains one or more water-solubilising groups such as sulfo groups or carboxyl groups.

If desired, the process according to the present invention may be conducted in a two-phase solvent system comprising water and a water-insoluble organic solvent, such a halogenated hydrocarbon, e.g. dichloromethane, or a $C_5$–$C_{12}$alcohol such as n-pentanol. In such two-phase reaction systems, optionally a phase transfer catalyst or a suitable surfactant may be present.

Preferably, however, the process according to the present invention is conducted in an anhydrous organic solvent, preferably in one or more of the following: alcohols; ketones; carboxylic acids; sulfones; N,N-tetrasubstituted ureas; N-alkylated lactams or N-dialkylated acid amides; ethers; aliphatic, cycloaliphatic or aromatic hydrocarbons, which may be optionally substituted with F, Cl or $C_1$–$C_4$alkyl; carboxylic acid esters and lactones; nitrites; and glymes.

Some specific examples of solvents are:
alcohols: methanol, ethanol, propanol, isopropanol, butanol, t-butanol, hexanol, heptanol, octanol, ethylene glycol and di-, tri- and tetra-ethylene glycol;

ketones: acetone, methylethylketone, methylisobutylketone and cyclohexanone; carboxylic acids: ethanoic acid, propanoic acid and chloroacetic acid;

sulfones: dimethylsulfone, diethylsulfone, tetramethylenesulfone, sulfolan and dimethylsulfoxide;

N,N-tetrasubstituted ureas: N-methylethyl-N'-methylethylurea, N-dimethyl-N'-dipropylurea, tetramethylurea, tetraethylurea, N,N'-dimethyl-N,N'-1, 3-propyleneurea, N,N'-dimethyl-N,N'-ethyleneurea;

N-alkylated lactams: N-methylpyrrolidone and N-ethylpyrrolidone;

N-dialkylated acid amides: N-dimethylformamide, N-diethylformamide and N-dimethylacetamide;

ethers: polyethylglycolether, di-,tri- and tetra-ethyleneglycoldimethylether, di-, tri- and tetra-ethyleneglycoldiethylether, terahydrofuran, dioxan, methyl-t-butylether, diethyleneglycolmonomethylether and ethyleneglycolmonomethylether;

aliphatic hydrocarbons: methylene chloride, pentane and hexane;

cycloaliphatic hydrocarbons: cyclohexane and decahydronaphthalene;

aromatic hydrocarbons: xylene, terahydronaphthalene and dichlorobenzene;

carboxylic acid esters: methyl benzoate, ethylacetate, γ-butyrolactone and n-butylacetate;

nitriles: acetonitrile, benzonitrile and phenylacetonitrile;

glymes: di-, tri- and tetra-glymes.

The process of the present invention is preferably conducted in the presence of a base which may be an organic base, an inorganic base or a mixture thereof and which is added prior to step B). The base is used as a buffer to neutralise mineral acid present during the formation of the diazonium salt reactants. The base may be used in at least equimolar amounts relative to the diazonium salt of formula (2) or (3) and preferably in an excess of up to 10 moles. Examples of suitable bases are Li—, Na—, K—, $NH_4$—, Mg—, Ca— and $NH(C_1$–$C_{18}$alkyl$)_3$-salts of carboxylic acids such as $C_1$–$C_4$carboxylic acids or benzoic acid. Specific examples of suitable bases are lithium-, potassium- or sodium acetate, -butyrate, -propionate and -stearate; barium- and calcium acetate; calcium propionate and -stearate; lithium- and sodium benzoate; ammonium acetate; and salts of acetic acid with triethylamine, tri-n-butylamine, tri-(2-ethylhexylamine), tri-n-octylamine and tri-n-dodecylamine. Preferred are alkaline metal acetates which form acetic acid as a desirable component in the arylation step B). Particularly preferred bases are sodium and potassium acetate, used in excess. The bases may also be used as salts in the catalyst generation, as described above.

The process of the present invention is preferably conducted at a temperature in the range of from −10 to 100° C., more preferably at a temperature in the range of from 0 to 80° C.

The following Examples further illustrate the present invention. Parts and percentages shown therein are by weight unless otherwise stated.

EXAMPLE 1

A) Synthesis of the Diazonium Compound

Into 150 g of 1-pentanol there are stirred 39 g of 2-aminobenzene sulfonic acid (90%) and 7 g of water and the reaction mixture is cooled to 10–15° C. At the same temperature, over 1 hour, 23.4 g of amyl nitrite are added, dropwise, to the reaction mixture and the whole is stirred for a further 2 hours. Finally, the nitrite excess is determined and the necessary amount of 2-aminobenzene sulfonic acid is added to remove the excess.

B) Reaction of the Diazonium Compound with a Divinyl Compound

The suspension from step A) is treated, with stirring and cooling, with 20 g of acetic anhydride and 32.4 g of sodium acetate. 1 g of palladium[bis(dibenzalacetone)]$_2$ is added and, after 5 minutes, 18.6 g of 4,4'-divinyl-biphenyl and 0.05 g of hydroquinone are added. The reaction mixture is then stirred at 20° C. for 5 hours, heated to 40° C. and held at this temperature for a further 5 hours.

The 1-pentanol solvent is removed by distillation, the resulting melt is dissolved in 300 mls of hot water at 90° C., the resulting solution is treated with 3 g of a filtration aid and the palladium compound is separated by filtration. Crystallisation of the reaction product from the filtered solution is induced by cooling the solution to 15° C. using a ramp. Finally, the product which crystallises out is separated by filtration, washed and dried. In this way, 40 g of the compound of formula (101) are obtained, representing a yield of 71% by weight, based on the weight of the 2-aminobenzene sulfonic acid starting material.

EXAMPLE 2

A) Synthesis of the Diazonium Compound 38 g of 3-amino-benzene sulfonic acid and 21.9 g of concentrated hydrochloric acid are stirred into 200 mls of water and the solution so obtained is cooled to 5° C. using ice. At the same temperature, over 1 hour, 42 g of a sodium nitrite solution (36%) are added, dropwise, and the whole is stirred for a further hour, during which time the temperature of the reaction mixture is held below 10° C. by the addition of ice. Finally, the nitrite excess is determined and the necessary amount of 3-aminobenzene sulfonic acid is added to remove the excess.

B) Reaction of the Diazonium Compound with a Divinyl Compound

The diazosulfone suspension from step A) is neutralised to pH 3-4 with 51 g of a 30% aqueous sodium hydroxide solution and then 20 g of sodium bicarbonate are added, with cooling and stirring. 1 g of palladium[bis(dibenzalacetone)]$_2$ is added and, after 5 minutes, 20.6 g of 4,4'-divinyl-biphenyl and 0.05 g of hydroquinone in 150 mls of dichloromethane are added. The emulsion so obtained is then stirred at 18–20° C. for 10 hours, heated to 40° C. and held at this temperature for a further 5 hours.

The solvent is removed by distillation, the solution so obtained is made up to 300 mls volume by adding water, heated to 90° C. and the palladium compound is separated by filtration. Crystallisation of the reaction product from the filtered solution is induced by cooling the solution to 15° C. using a ramp. Finally, the product which crystallises out is separated by filtration, washed and dried. In this way, 40 g of the compound of formula:

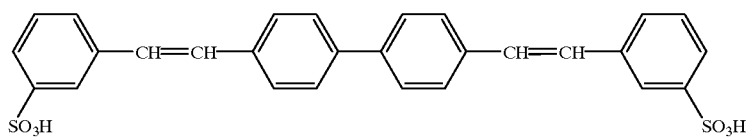

(102)

are obtained, representing a yield of 79% by weight, based on the weight of the 4,4'-divinyl-biphenyl starting material.

EXAMPLE 3

A) Synthesis of the Diazonium Compound 42 g of technical quality 2-aminobenzene sulfonic acid (38 g of 100% active material) and 13.8 g of concentrated sulfuric acid (96%) are stirred into 150 g of anhydrous acetic acid and the whole is cooled externally to 5–10° C. At the same temperature, over 1 hour, 31.7 g of a sodium nitrite solution (50%) are added, dropwise, and the whole is stirred for a further hour, during which time the temperature of the reaction mixture is held below 10° C. Finally, the nitrite excess is determined and the necessary amount of 2-aminobenzene sulfonic acid is added to remove the excess.

B) Reaction of the Diazonium Compound with a Divinyl Compound

To the product of step A), there are added 200 g acetic anhydride, dropwise, over 3 hours, whereupon a weakly exothermic reaction occurs. The reaction mixture is stirred for 1 hour, 32.8 g of anhydrous sodium acetate are added, with good stirring, 1 g of palladium[bis(dibenzalacetone)]$_2$ is added and, after 5 minutes, 20.6 g of 4,4'-divinyl-biphenyl and 0.05 g of hydroquinone in 150 mls of dichloromethane are added. The mixture so obtained is then stirred at 18–20° C. for 10 hours, heated to 40° C. and held at this temperature for a further 5 hours.

The acetic acid is distilled off under vacuum and the resulting melt is made up to 300 mls with water. The resulting mixture is heated to 90° C. and insoluble components are separated by filtration. Crystallisation of the reaction product from the filtered solution is induced by cooling the solution to 15° C. using a ramp. Finally, the product which crystallises out is separated by filtration, washed and dried. In this way, 48 g of the compound of formula (101) are obtained, representing a yield of 83% by weight, based on the weight of the 4,4'-divinyl-biphenyl starting material.

We claim:
1. A process for the production of a compound of formula:

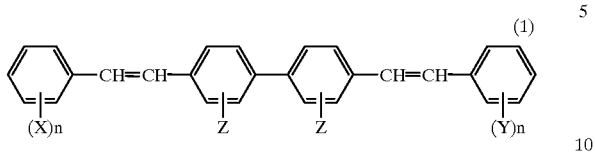  (1)

in which X and Y, independently, are hydrogen, halogen, NO$_2$, CF$_3$, CN, C$_1$–C$_4$alkyl, C$_1$–C$_4$alkoxy, COO—C$_1$–C$_4$alkyl, CO—C$_1$–C$_4$alkyl, NH—(C$_1$–C$_4$alkyl), N(C$_1$–C$_4$alkyl)$_2$, NH(C$_1$–C$_4$alkyl-OH), N(C$_1$–C$_4$alkyl-OH)$_2$, COOH or SO$_3$H or an ester or amide thereof, or COOM or SO$_3$M in which M is Na, K, Ca, Mg, ammonium, mono-, di-, tri- or tetra-C$_1$–C$_4$alkylammonium, mono-, di- or tri-hydroxyalkylammonium or ammonium that is di- or tri-substituted with a mixture of C$_1$–C$_4$alkyl and C$_1$–C$_4$hydroxyalkyl groups;

Z is hydrogen, C$_1$–C$_4$alkyl, C$_1$–C$_4$alkoxy, CF$_3$, halogen (F, Cl, Br, I), SO$_3$H or SO$_3$M in which M has its previous significance; and n is 1 or 2; comprising A) diazotising one mole of an amine of formula:

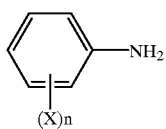  (2A)

in which X and n have their previous significance, to produce a diazonium compound having the formula:

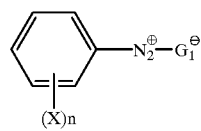  (2)

in which X and n have their previous significance and G$_1$ is a counter ion; and diazotising one mole of an amine of formula:

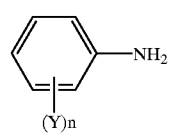  (3A)

in which Y and n have their previous significance, to produce a diazonium compound having the formula:

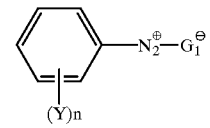  (3)

in which Y, n and G$_1$ have their previous significance; and

B) reacting one mole of a divinyl compound having the formula:

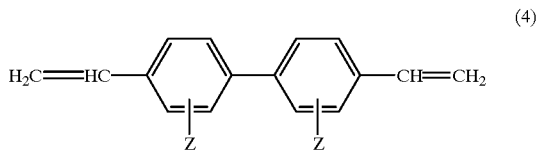  (4)

in which Z has its previous significance, with one mole of a compound having the formula (2) and with one mole of a compound having the formula (3), in the presence of an inorganic or organic palladium salt, or a mixture thereof, as catalyst-precursor.

2. A process according to claim 1 in which step B) is conducted without intermediate isolation of the reactants of formula (2) and (3).

3. A process according to claim 1 in which steps A) and B) are conducted simultaneously by controlled addition of the respective reactants.

4. A process according to claim 1 in which X and Y, independently, are hydrogen, cyano, COOM or SO$_3$M in which M is as defined in claim 1.

5. A process according to claim 1 in which Z is hydrogen.

6. A process according to claim 1 in which n is 1.

7. A process according to claim 1 in which G$_1$ is H$_2$PO$_4^-$, HPO$_4^{2-}$, NO$_3^-$, CF$_3$COO$^-$, $^-$OOC—COO$^-$ (oxalate), Cl$_3$CCOO$^-$, ClCH$_2$COO$^-$, I$^-$, Cl$^-$, Br$^-$, F$^-$, ClO$_4^-$, PF$_6^-$, BF$_4^-$, Oac$^-$, HSO$_4^-$, SO$_4^{2-}$, CH$_3$(C$_6$H$_4$)SO$_3^-$ or CH$_3$SO$_3^-$.

8. A process according to claim 7 in which G$_1$ is H$_2$PO$_4^-$, Cl$_3$CCOO$^-$, ClCH$_2$COO$^-$, PF$_6^-$, BF$_4^-$, Oac$^-$, HSO$_4^-$, SO$_4^{2-}$, CH$_3$(C$_6$H$_4$)SO$_3^-$ or CH$_3$SO$_3^-$.

9. A process according to claim 1 in which the compound (3) is identical to the compound (4) so that the compound of formula (1) obtained is symmetrical.

10. A process according to claim 1 in which the compound of formula (2) is 4,4'-divinyl-biphenyl.

11. A process according to claim 1 in which the compound of formula (3) and (4) is 2-diazobenzene sulfonic acid.

12. A process according to claim 11 in which the compound of formula (1) obtained has the formula:

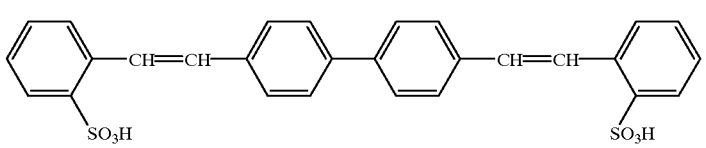

(101)

or an alkali metal salt thereof.

13. A process according to claim 1 in which the compound of formula (3) and (4) is 3-diazobenzene sulfonic acid.

14. A process according to claim 13 in which the compound of formula (1) obtained has the formula:

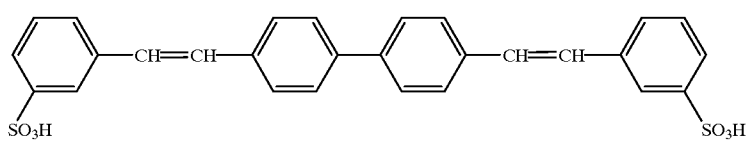

(102)

or an alkali metal salt thereof.

15. A process according to claim 1 in which the palladium catalyst precursor used in step A) is generated, in situ or ex situ, by reduction of a palladium (II) compound, optionally in the presence of a salt and optionally in the presence of a ligand-forming or colloid-stabilising compound.

16. A process according to claim 15 in which the palladium (II) compound is $PdCl_2$, $PdBr_2$, $Pd(NO_3)_2$, $H_2PdCl_4$, $Pd(OOCCH_3)_2$, $[PdCl_4]Na_2$, $[PdCl_4]Li_2$, $[PdCl_4]K_2$, palladium(II)acetylacetonate, dichloro-(1,5-cyclooctadiene) palladium(II), dichlorobis-(acetonitrile)palladium(II), dichlorobis-(benzonitrile)palladium(Ii), π-allylpalladium(II) chloride dimer, bis-(π-methallyl palladium(II)chloride) or π-allylpalladium(II)acetylacetonate.

17. A process according to claim 15 in which the ligand-forming compound is one or more of an olefin having the formula $CHR_2\!=\!CHR_3$ in which $R_2$ is H, F, Cl, Br or $-COOR_4$ (in which $R_4$ is H or $C_1-C_4$alkyl) and $R_3$ is $-COO(C_1-C_4\text{alkyl})$, $-COR_4$ or $C_1-C_2$alkyl optionally substituted by halogen; dibenzylideneacetone (dba), optionally substituted with halogen (F, Cl or Br), $SO_3M$ (in which M is as defined in claim 1), $C_1-C_4$alkyl or $C_1-C_4$alkoxy in the benzene rings; a phosphite of formula $P(OR_5)$ in which $R_5$ is e.g. phenyl, $C_1-C_6$alkyl or a partially or perfluorinated $C_1-C_6$alkyl; or CO.

18. A process according to claim 15 in which the reduction is effected using, as reducing agent, CO, $H_2$, a formate, a primary or secondary $C_1-C_8$alkanol, hydrazine, an amine, a mixture of CO with an alkanol or water, or the ligating olefine per se.

19. A process according to claim 15 in which the catalyst is added as $Pd(dba)_2$, $Pd(dba)_3$.solvent, $Pd_2(dba)_3$ or $Pd_2(dba)_3$.solvent.

20. A process according to claim 15 in which the palladium catalyst is used in an amount of 0.01 to 5 mole %, based on the diazonium salt of formula (2) or (3).

21. A process according to claim 15 in which, after completion of the process, the palladium catalyst is recovered for re-use.

22. A process according to claim 1 in which the process is effected in water, as solvent.

23. A process according to claim 1 in which the process is conducted in a two-phase solvent system comprising water and a water-insoluble organic solvent.

24. A process according to claim 1 in which the process is effected in an anhydrous organic solvent.

25. A process according to claim 24 in which the anhydrous organic solvent is an alcohol; a ketone; a carboxylic acid; a sulfone; an N,N-tetrasubstituted urea; an N-alkylated lactam or N-dialkylated acid amide; an ether; an aliphatic, cycloaliphatic or aromatic hydrocarbon, which may be optionally substituted with F, Cl or $C_1-C_4$alkyl; a carboxylic acid ester or lactone; a nitrile; or a glyme.

26. A process according to claim 1 in which the reaction temperature ranges from −10 to 100° C.

27. A process according to claim 26 in which the reaction temperature ranges from 0 to 80° C.

28. A process according to claim 1 in which the process is conducted in the presence of a base which is added prior to step B).

29. A process according to claim 28 in which the base is an organic base, an inorganic base or a mixture thereof.

30. A process according to claim 29 in which the base is a Li—, Na—, K—, $NH_4$—, Mg—, Ca— and $NH(C_1-C_{18}\text{alkyl})_3$-salt of a carboxylic acid.

31. A process according to claim 30 in which the carboxylic acid is a $C_1-C_4$carboxylic acid or benzoic acid.

32. A process according to claim 30 in which the base is lithium-, potassium- or sodium acetate, -butyrate, -propionate or -stearate; barium- or calcium acetate; calcium propionate or -stearate; lithium- or sodium benzoate; ammonium acetate; or a salt of acetic acid with triethylamine, tri-n-butylamine, tri-(2-ethylhexylamine), tri-n-octylamine or tri-n-dodecylamine.

33. A process according to claim 32 in which the base is an alkaline metal acetate which forms acetic acid as a component in the arylation step B).

34. A process according to claim 33 in which the alkaline metal acetate is sodium or potassium acetate.

35. A process according to claim 31 in which the base is used in at least equimolar amounts relative to the diazonium salt of formula (2) or (3).

36. A process according to claim 35 in which the base is used in an excess of up to 10 moles, relative to the diazonium salt of formula (2) or (3).

* * * * *